United States Patent [19]

Robbins et al.

[11] 4,122,196

[45] Oct. 24, 1978

[54] PROCESS FOR THE MANUFACTURE OF YEAST GLYCAN

[75] Inventors: Ernest Aleck Robbins, High Ridge; Robert Dudley Seeley, Crestwood, both of Mo.

[73] Assignee: Anheuser-Busch, Incorporated, St. Louis, Mo.

[21] Appl. No.: 710,783

[22] Filed: Aug. 2, 1976

Related U.S. Application Data

[63] Continuation-in-part of Ser. No. 524,653, Nov. 18, 1974, abandoned.

[51] Int. Cl.$^2$ .............................................. A23J 1/18
[52] U.S. Cl. .................................... 426/60; 426/656; 426/431; 195/4; 195/7; 195/105
[58] Field of Search ...................... 195/4, 5, 7, 74, 82, 195/105; 426/60, 61, 656, 431

[56] References Cited

U.S. PATENT DOCUMENTS

| | | | |
|---|---|---|---|
| 3,867,255 | 2/1975 | Newell et al. | 195/5 |
| 3,867,554 | 2/1975 | Sucher et al. | 426/60 |
| 3,947,605 | 3/1976 | Chao | 426/60 X |
| 3,975,553 | 8/1976 | Griffan | 195/74 X |
| 3,991,215 | 11/1976 | Robbins | 195/5 X |

*Primary Examiner*—Raymond N. Jones
*Assistant Examiner*—Esther M. Kepplinger
*Attorney, Agent, or Firm*—Gravely, Lieder & Woodruff

[57] ABSTRACT

A process for making a useful product from yeast cell walls is disclosed. The process involves autolysis of whole yeast cells followed by separation of the insoluble cellular debris which is homogenized, extracted, and again separated into solubles and insolubles fractions. The insolubles fraction is edible when purified and increases the viscosity of aqueous solutions while imparting a fat-like mouthfeel to the same. The insolubles fraction is called yeast glycan.

14 Claims, 1 Drawing Figure

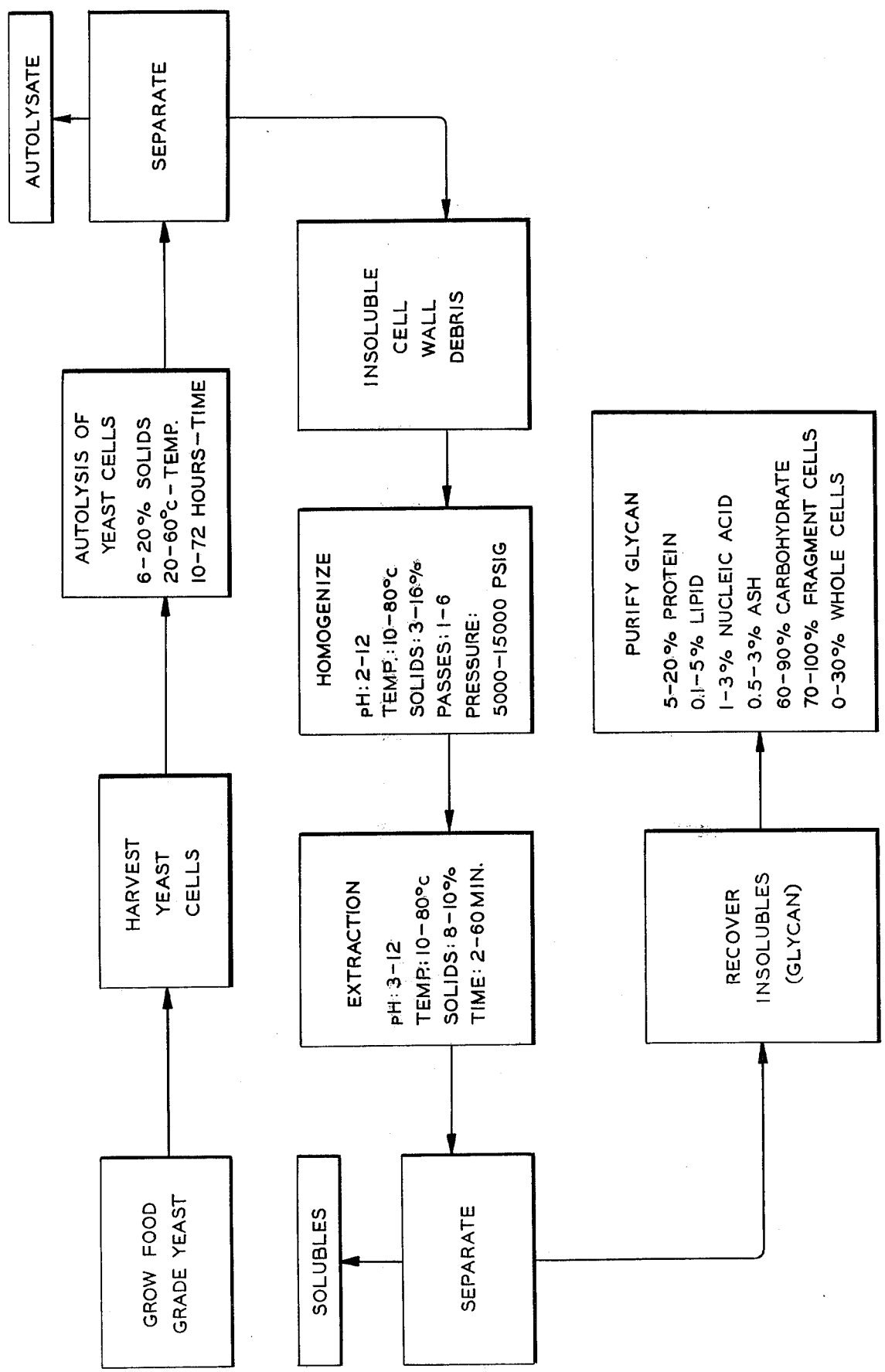

PROCESS FOR THE MANUFACTURE OF YEAST GLYCAN

REFERENCE TO PRIOR APPLICATIONS

This application is a continuation-in-part of prior copending application of Robbins and Seeley filed Nov. 18, 1974 as Ser. No. 524,653 now abandoned.

BACKGROUND OF THE INVENTION

Residual yeast from brewing operations and yeast produced as baker's yeast have long been used in foods as a source of vitamins, minerals, and protein. The levels of dried yeasts used in food products has never generally exceeded more than 5% because dried food yeasts have no functional value for food processing, and, at higher levels, contribute a distinct taste to the food product.

Extracts of yeast have long been used as a source of flavor. Extracts of yeast are sometimes classified into autolysates, plasmolysates, and hydrolysates according to their method of preparation. Hydrolysates are prepared by the controlled cooking of yeast in acid solution. Plasmolysates are prepared by extracting the cellular materials from the yeast cell with high concentrations of salt, sugar, or certain acetate esters. Autolysates are prepared by inducing the self-digestion of the cytoplasmic materials in the whole cell followed by recovery of the solubilized material. By any method, an insoluble residue is also obtained. This insoluble residue contains the extracted and washed yeast cell debris. This debris, which is usually discarded as a waste product contains the walls of the yeast cell, and usually protein, nucleic acid, and lipid components.

We have discovered a method of reclaiming a valuable food product from this cellular debris. This product has bland flavor, and unique functional characteristics. We call this product glycan.

One of the primary functional characteristics of this product is its ability to hold water and give thickening properties to aqueous food system. We have further discovered that the addition of this product to liquid food systems gives the food product a "fat-like" mouthfeel even when these products contain little or no fat. This is very useful in formulating low-calorie products. The product obtained from the insoluble residues of yeast has all of the desirable attributes of the product described in copending application of Sucher, Robbins, Sidoti, Schuldt and Seeley entitled YEAST GLYCAN AND PROCESS OF MAKING SAME Ser. No. 310,452 filed Nov. 29, 1972, U.S. Pat. No. 3,867,554 issued Feb. 18, 1975. The glycan described in that application and the glycan described herein both consist of the fragmented cell walls of yeast, but are obtained by different processes.

We have discovered that a satisfactory glycan preparation can be obtained from the insoluble residue remaining from the autolysis process. This insoluble residue can be obtained from the autolysis of baker's yeast, brewer's yeast, or a mixture thereof.

SUMMARY OF THE INVENTION

Our invention comprises the following steps: autolysis of whole yeast cells, separation of the insoluble cellular debris from the soluble fraction (hereinafter called the autolysate), comminution of the insoluble cellular debris, extraction of the comminuted insoluble cellular debris, recovery, and purification of the remaining insoluble debris (which is called glycan).

The invention further comprises the processes and products hereinafter described and claimed. The drawing is a schematic flow sheet of the process of this invention. Whole yeast cells (biomass) are produced by methods known to those versed in the art. We preferably use biomass of strains of Saccharomyces and Candida grown on food grade nutrients in batch and continuous fermentation. However, the main considerations are that the yeast be of food grade and produced in good yield.

The biomass is harvested by centrifugation or filtration and water washed. When necessary, dilute alkali may be incorporated in the wash to remove adhering color and taste bodies.

DETAILED DESCRIPTION

The whole yeast cells then are autolyzed by methods known to those versed in the art. The autolytic process depends upon the enzyme systems of the yeast. Therefore, autolysis is applicable to fresh yeast and not applicable to dried yeast wherein the enzyme systems have been destroyed. Autolysis is usually accomplished by incubating yeast at about 6% to about 20% solids, about 20° C. to about 60° C., for about 10 hours to about 72 hours. Autolysis is usually facilitated by the addition of salt or acetate esters. The autolysis conditions employed to generate the data reported herein are:

| | |
|---|---|
| Solids | 8-10% |
| pH | 5-8 |
| Temp. | 40-60%° C |
| Time | 24-30 hours |
| Ethyl Acetate | 1% v/v |

The insoluble cellular debris is recovered by centrifugation. The insoluble cellular debris recovered at this stage does not have the desired ability to thicken food systems, and is highly flavored. Aqueous washing of the insoluble cellular debris removes some of the flavor, but does not improve the thickening ability.

However, if the insoluble cellular debris is comminuted, extracted with water preferably under slightly alkaline conditions, and recovered, the insoluble cellular debris has the desired ability to thicken aqueous food systems and has a bland flavor.

The comminution is achieved by repeated passages through a Manton-Gaulin homogenizer. More than one pass is needed in order to obtain maximum release of the unwanted constituents during the subsequent alkali extraction. The number of passes through the homogenizer and the pressure, the temperature and solids content of the material being homogenized, and the time, temperature, and pH of extraction influence the release of unwanted constituents from the cellular debris. The release of the unwanted constituents is determined by measuring the amount of nitrogenous material released. The data are presented in Table I. The data of Table I show that adequate homogenization and extraction can occur under the conditions:

| | |
|---|---|
| pH | 2-12 |
| Temp. | 10-80° C |
| Solids | 3-16% |
| Passes through homogenizer | 1-6 |

| | -continued | |
|---|---|---|
| Pressure | 5000-15000 psig | |

The conditions of extraction are as follows:

| pH | 3-12 |
|---|---|
| Temp. | 10-80° C |
| Solids | 8-10% |
| Time | 2-60 minutes |

TABLE I

| pH of Homogenization | pH of Extraction | Homogenizer Passes | % Protein | Viscosity* |
|---|---|---|---|---|
| 2.0 | 9.5 | 3 | 33.13 | 9,000 |
| 4.0 | 9.5 | 3 | 38.66 | 10,000 |
| 6.0 | 9.5 | 3 | 34.14 | 10,400 |
| 8.0 | 9.5 | 3 | 30.34 | 13,600 |
| 10.0 | 9.5 | 3 | 33.47 | 14,976 |
| 6.0 | 4.0 | 3 | 63.89 | 13,000 |
| 6.0 | 6.0 | 3 | 28.38 | 11,700 |
| 6.0 | 8.0 | 3 | 23.98 | 12,800 |
| 6.0 | 10.0 | 3 | 21.27 | 12,600 |
| 6.0 | 9.5 | 0 | 68.09 | 33 |
| 6.0 | 9.5 | 1 | 26.66 | 9,500 |
| 6.0 | 9.5 | 2 | 21.66 | 11,600 |
| 6.0 | 9.5 | 3 | 20.66 | 13,300 |
| 6.0 | 9.5 | 4 | 20.38 | 13,200 |
| 6.0 | 9.5 | 5 | 19.49 | 15,700 |

*Maxium viscosity (centipoise) of a 10% suspension at 25° C.

The comminuted, extracted cellular debris is water washed. The washed material is called glycan. The glycan product has the composition of about 5% to about 20% crude protein, about 0.1% to about 5% lipid, about 1% to about 3% nucleic acid, about 0.5% to about 3.0% ash, and from about 60% to about 95% carbohydrate. The yeast glycan produces a viscosity of at least about 500 centipoise when suspended in a 10% aqueous solution by weight at a temperature of 25° C. It is composed mainly of irregularly shaped fragmented cells and cell walls (from about 70 to 100% by weight), with a lesser amount (0 to 30%) of whole cells containing methylene blue stainable material.

The growing of the yeast is conventional in the art and following is a typical yeast grow-up procedure.

PREPARATION OF YEAST BIOMASS FROM BAKER'S YEAST

The yeast SACCHAROMYCES CEREVISIAE (Baker's yeast) was inoculated into 10 ml. of sterile glucose peptone yeast extract broth and incubated 2 days at 30° C. This broth culture was used to inoculate 1 liter of sterile molasses broth of the following composition; clarified cane and beet molasses reducing substance by Munson Walker gravimetric method, 30.0 g.; ammonium sulfate, 4.55 g.; diammonium phosphate, 0.68 g.; potassium sulfate, 0.20 g.; magnesium heptahydrate, 60 mg. The 1 liter of molasses broth was contained in a 4 liter Ehrlenmeyer flask. The reaction was adjusted to pH 5.2 by the addition of sulfuric acid before sterilization in the autoclave. This molasses broth growth stage was called the primary stage. After inoculation it was incubated for 3 days at 30° C on a rotary shaker revolving at 112 RPM with a 4inch eccentric throw.

Primary stage yeast growth equal to 5.0 g. dry substance yeast was used to stock a small fermentor containing 3.2 liters of potable water. This was called Stage 1. Immediately, a liquid feed was supplied to the water suspension of yeast. The liquid feed comprised two solutions. Solution 1 contained 150 g. clarified cane and beet molasses reducing substance equivalent by Munson Walker gravimetric method diluted to 1 liter with portable water. Solution 2 contained 29.9 ml. of 29% ammonia, 12.8 g. ammonium sulfate, and 2.58 ml. of 85% phosphoric acid in a volume of 1 liter potable water. The liquid feed was delivered continuously for 11 hours at an hourly increasing rate of 1.14. The temperature of the growth broth was 35° C. Aeration was provided at a rate of 3 volumes air per volume of growth broth per minute using a sparger and impellor system. The reaction was maintained at pH 5.0-7.0.

Stage 1 produced yeast dry substance equivalent to 54.3 percent of the molasses provided. This Stage 1 yeast contained 8.69% N and 1.3% P.

Stage 1 yeast was used to stock Stage 2. Stage 2 liquid feed comprised two solutions. Solution 1 contained 150 g. clarified cane and beet molasses reducing substances equivalent by Munson Walker gravimetric method. Solution 2 contained 33.3 ml. 29% ammonia, 17.3 g. ammonium sulfate, and 3.34 ml. of 85% phosphoric acid. Stage 2 was stocked with 16.4 g. d.s. of Stage 1 yeast by adding the Stage 1 yeast to 3.2 liters of potable water contained in a small fermentor. The liquid feed was delivered immediately and continuously for 11 hours at an hourly increasing rage of 1.14. The reaction of the growth broth was between 5.5 and 6.8. The growth broth temperature was 35° C. Aeration was provided at a rate of 3 volumes of air per volume of growth broth using a sparger and impellor system.

Stage 2 produced yeast dry substance equivalent to 30 grams of the weight of the clarified molasses reducing substance per liter dry solids yeast. The Stage 2 yeast contained 8.03% N and 1.12% P.

The yeast was separated from the beer by centrifugation and washed three times with water.

The preparation of glycan from the insoluble cellular debris of autolyzed yeast is shown in the following examples.

EXAMPLE NO. 1

Preparation of Yeast Glycan from Baker's Yeast 1500 grams of a slurry of commercial baker's yeast produced according to the procedure hereinbefore set out and containing 120 grams of dry solids including 40 grams of carbohydrate were autolyzed by incubating at 50° C., for 24 hours with 1% v/v ethyl acetate and with gentle agitation.

The autolysate was centrifuged at 9000 rcfg to obtain the insoluble cellular debris, hereinafter called autolyzed yeast residue. This autolyzed yeast residue contains 42.6 grams of solids. The supernate contains 57.4 grams of solids. The autolyzed yeast residue produced 0 centipoise viscosity at the 10% level at 25° C.

The autolyzed yeast residue was resuspended to 5% solids in water at a pH 5.0, chilled to 10° C., and passed three times through a Manton-Gaulin homogenizer at 9000 psig with cooling to 10° C between each pass.

The comminuted autolyzed yeast residue was adjusted to pH 9.5 by the addition of alkali (2.8 grams NaOH), and gently agitated for 60 minutes at 26° C. The comminuted, extracted autolyzed yeast residue was recovered by centrifugation at 9000 rcfg, resuspended in 600 ml. water, and centrifuged again to obtain the glycan. The slurry of glycan contained 28.1 grams of solids for a yield of 21 pounds of glycan solids per 100 pounds of starting yeast. The slurry of glycan produced a 15,000 centipoise viscosity when tested at the 10% level at 25° C. The composition (dsb) is: 73.7% carbohydrate, 20.4% crude protein (N × 6.25), 2.4% nucleic acid, 1.0% ash.

EXAMPLE NO. 2

Preparation of Glycan from a Mixture of Brewer's and Baker's Yeast

Brewer's yeast was first debittered by washing with tap water thrice, then NaOH was added to a 5% suspension at the rate of 2.0 gl/1. The alkaline suspension was stirred at room temperature for 30 minutes and then centrifuged. The residue was washed three times with water.

The debittered brewer's yeast was mixed with baker's yeast at a ratio of 2:1. A 9.0% suspension containing 66.7 grams of brewer's yeast and 33.3 g. of baker's yeast was prepared. Ethyl acetate was added to a concentration of 1.0%, and the suspension was heated, with continuous stirring, at 50° C, for 24 hours. To remove the ethyl acetate, the suspension was heated to 95° C. for 5 minutes, and then cooled. The suspension was then centrifuged, and the autolyzed yeast residue was used as the source of glycan. This residue has a viscosity of 0 centipoise at 10% solids.

This residue was first homogenized at a 5% total solids concentration by passing three times through a Manton-Gaulin homogenizer at a pressure of 10,000 psig. The homogenate was adjusted to pH 9.5 with NaOh, and then stirred at room temperature for 60 minutes. The alkaline soluble material was removed by centrifugation and the residue was washed three times with water. The washed residue was treated with $H_2O_2$ (1 g./100 g. solids) in order to white the color thereof. Residual $H_2O_2$ was destroyed with a catalase treatment, and the final glycan residue was spun down.

The glycan contained 18% protein, 3% lipid, 2.4% nucleic acids, 1.2% ash, and 77.4% carbohydrate on a solids basis. The viscosity of a 10% suspension was 23,000 cps at 25° C.

EXAMPLE NO. 3

Preparation of Glycan from Spent Brewer's Yeast

Spent brewer's yeast (2,500 gm at 13.57% solids, reflectance 58.5%) was diluted with 2,500 ml of cold water and adjusted to pH 3.5 with 4 ml of 5.8 N HCl. The mixture at 6.6% solids was screened on a 100 mesh screen to remove large particles of non-yeast material. Screened material (4,795 gm) was mixed with 12.2 liters of cold water to give a mixture of 1.9% solids. The mixture was adjusted from pH 4 to pH 4.85 with 3.5 ml 5 N NaOH.

The yeast flocculated and settled rapidly. After 15 minutes the slightly turbid yellow supernatant liquor was removed by aspiration. The yeast sediment amounted to 3,890 gm at 5.6% solids and 52.3% protein (dsb). The sediment was centrifuged for 10 minutes at 12,000 xg. The precipitate was resuspended in water to give a yeast preparation at 9.2% solids and 52.3% protein (dsb). The yeast (2,208 gm) was mixed with 22.5 ml ethyl acetate and 4.4 ml toluene. The mixture was held for 48 hours at 40° C and pH 6.0. After 48 hours, the mixture was heated to 70° C and 2,190 gm was centrifuged at 12,000 xg for 10 minutes to give 1,594 ml of autolyzed yeast extract (solubles) and 353 gm of autolysis residue (precipitate). The precipitate was mixed with 200 ml water and centrifuged. The precipitate was resuspended in water to give washed autolysis residue at 10% solids and 24.6% crude protein (dsb). This mixture showed a Brookfield viscosity of 0 cps. The autolysis residue was further diluted to 5.3% solids and adjusted from pH 6.1 to 12.0 with NaOH. The pH 12 material was homogenized three passes at 9,000 psig using a Manton-Gaulin Homogenizer. The material was chilled between homogenizer passes. The homogenate was heated to 70° C and adjusted from pH 11.6 to pH 12 using NaOH. The pH 12 homogenate (1,055 gm) was centrifuged 10 minutes at 12,000 xg to give 685 ml of a brown turbid supernatant solution at 3.95% solids and 32.8% protein (dsb). The precipitate was water washed three more times by suspending in water and centrifuging. Prior to the final wash, the resuspended material was adjusted to pH 6.5 with hydrochloric acid.

The glycan contained 15.8% protein on a solids basis. The viscosity of a 5% suspension was 13,100 cps.

What we claim is:

1. A process for the production of yeast glycan comprising the steps of:
   A. autolyzing live yeast cells,
   B. separating the autolyzed yeast cells into solubles fraction and an insoluble cellular debris fraction which contains unwanted constituents whereby the debris fraction does not have the desired ability to thicken food systems and is highly flavored,
   C. comminuting the insoluble cellular debris fraction in an aqueous system,
   D. extracting said unwanted constituents from the comminuted cellular debris fraction in an aqueous system at a pH from about 3 to about 12, a temperature of about 10° to about 80° C for up to about 60 minutes to yield a solubles portion and an insolubles portion from which said unwanted constituents have been released,
   E. separating the solubles portion from the insolubles portion of the extracted cellular debris fraction, and
   F. recovering the insolubles portion as yeast glycan.

2. The process of claim 1 wherein the yeast is selected from the group consisting of baker's yeast, brewer's yeast, and mixtures thereof.

3. The process of claim 1 wherein the autolysis is at about 6% to about 20% solids and a temperature of about 20° to about 60° C for about 10 to about 72 hours.

4. The process of claim 3 wherein the autolysis occurs in the presence of about 1% of a salt or acetate ester.

5. The process of claim 4 wherein the ester is ethyl acetate.

6. The process of claim 1 wherein the comminution of the insoluble cellular material is by homogenization.

7. The process of claim 6 wherein the homogenization is at a pH of about 2 to about 12, a temperature of about 10° to about 80° C., a solids content of about 3% to about 16%, a pressure of about 5000 to about 15,000 psig, and the material is passed through the homogenizer about one to about six times.

8. The process of claim 1 wherein the extraction of the comminuted cellular material is at a solids content of about 8% to about 10% for about 2 minutes to about 60 minutes.

9. The process of claim 1 wherein the recovered glycan has a composition of about 5% to about 20% protein, about 0.1% to about 5% lipid, about 1% to about 3% nucleic acid, about 0.5 to about 3% ash, and about 60% to about 90% carbohydrate.

10. The process of claim 9 wherein the glycan has about 70% to about 100% fragmented cells, and about 0% to about 30% whole cells containing methylene blue stainable material.

11. The process of claim 1 wherein the extraction of the comminuted cellular material is at an alkaline pH.

12. The process of claim 1 wherein the extraction of the comminuted cellular material is at a pH of about 9.5 to about 12.

13. A process for the production of yeast glycan comprising the steps of:
   A. autolyzing live yeast cells,
   B. separating the autolyzed yeast cells into solubles fraction and an insoluble cellular debris fraction which contains unwanted constituents whereby the debris fraction does not have the desired ability to thicken food systems and is highly flavored,
   C. comminuting the insoluble cellular debris fraction in an aqueous system at a pH of about 2 to about 12 and a temperature of about 10° to about 80° C and a solids content of about 3% to about 16%,
   D. extracting said unwanted constituents from the comminuted cellular debris fraction in an aqueous system at an alkaline pH, a temperature of about 10° to about 80° C, for up to about 60 minutes to yield a solubles portion and an insolubles portion from which said unwanted constituents have been released,
   E. separating the solubles portion from the insolubles portion of the extracted cellular debris fraction, and
   F. recovering the insolubles portion as yeast glycan.

14. The process of claim 13 wherein the extraction of the comminuted cellular material is at a pH of about 9.5 to about 12.

* * * * *